United States Patent
Michelson

(10) Patent No.: US 7,163,561 B2
(45) Date of Patent: *Jan. 16, 2007

(54) FLANGED INTERBODY SPINAL FUSION IMPLANTS

(75) Inventor: Gary K. Michelson, Venice, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/838,933

(22) Filed: May 4, 2004

(65) Prior Publication Data

US 2004/0210314 A1    Oct. 21, 2004

Related U.S. Application Data

(63) Continuation of application No. 09/903,141, filed on Jul. 10, 2001, now Pat. No. 6,730,127.

(60) Provisional application No. 60/217,004, filed on Jul. 10, 2000.

(51) Int. Cl.
   - A61F 2/44 (2006.01)
   - A61F 2/30 (2006.01)
   - A61B 17/56 (2006.01)
   - A61B 17/58 (2006.01)

(52) U.S. Cl. .................. 623/17.16; 623/17.11; 623/908; 606/60; 606/61

(58) Field of Classification Search ............ 623/17.11, 623/17.16, 908, 17.12, FOR. 113; 606/60–61, 606/69
See application file for complete search history.

(56) References Cited

U.S. PATENT DOCUMENTS

| | | |
|---|---|---|
| 4,349,921 A | 9/1982 | Kuntz |
| 4,743,256 A | 5/1988 | Brantigan |
| 4,917,704 A | 4/1990 | Frey et al. |
| 4,955,908 A | 9/1990 | Frey et al. |
| 5,520,664 A | 5/1996 | Bricault et al. |
| 5,522,899 A * | 6/1996 | Michelson ................ 606/61 |

(Continued)

FOREIGN PATENT DOCUMENTS

EP    0 179 695    4/1986

(Continued)

Primary Examiner—Henry Bennett
Assistant Examiner—Kiandra C. Lewis
(74) Attorney, Agent, or Firm—Martin & Ferraro, LLP

(57) ABSTRACT

A flanged interbody spinal fusion implant for insertion at least in part between adjacent vertebral bodies has opposed upper and lower surfaces adapted to contact each of the adjacent vertebral bodies from within the disc space, a leading end for insertion between the adjacent vertebral bodies, and a trailing end opposite the leading end. The trailing end has a height greater than the maximum height of the disc space forming a flanged portion adapted to overlie a part of the anterior aspects of the vertebral bodies adjacent and proximate the disc space to be fused. The flanged portion has at least two bone screw receiving holes, at least one each adapted to overlie each of the adjacent vertebral bodies at least in part. The implant has at least one locking element to lock one or more of the bone screws inserted in the bone screw receiving holes. Instrumentation for inserting the implant, forming screw holes in the vertebral body, and for locking the locking elements are disclosed.

67 Claims, 12 Drawing Sheets

U.S. PATENT DOCUMENTS

| | | |
|---|---|---|
| 5,534,031 A | 7/1996 | Matsuzaki et al. |
| 5,674,296 A | 10/1997 | Bryan et al. |
| 5,713,899 A | 2/1998 | Marnay et al. |
| 5,782,919 A | 7/1998 | Zdeblick et al. |
| 5,865,846 A | 2/1999 | Bryan et al. |
| 5,868,745 A | 2/1999 | Alleyne |
| 5,888,223 A | 3/1999 | Bray, Jr. |
| 5,904,683 A | 5/1999 | Pohndorf et al. |
| 5,906,573 A | 5/1999 | Aretz |
| 6,066,175 A | 5/2000 | Henderson et al. |
| 6,093,205 A | 7/2000 | McLeod et al. |
| 6,113,637 A | 9/2000 | Gill et al. |
| 6,193,721 B1 | 2/2001 | Michelson |
| 6,231,610 B1 | 5/2001 | Geisler |
| 6,235,059 B1 | 5/2001 | Benezech et al. |
| 6,306,170 B1 | 10/2001 | Ray |
| 6,342,055 B1 | 1/2002 | Eisermann et al. |
| 6,402,755 B1 | 6/2002 | Pisharodi |
| 6,432,106 B1 | 8/2002 | Fraser |
| 6,447,546 B1 | 9/2002 | Bramlet et al. |
| 6,461,359 B1 | 10/2002 | Tribus et al. |
| 6,471,724 B1 | 10/2002 | Zdeblick et al. |
| 6,500,205 B1 | 12/2002 | Michelson |
| 2004/0068318 A1* | 4/2004 | Coates et al. ............ 623/17.11 |
| 2004/0102848 A1* | 5/2004 | Michelson ............... 623/17.11 |
| 2004/0176776 A1* | 9/2004 | Zubok et al. ................. 606/96 |
| 2004/0193272 A1* | 9/2004 | Zubok et al. ............ 623/17.11 |
| 2004/0199253 A1* | 10/2004 | Link et al. ............... 623/17.11 |
| 2005/0033433 A1* | 2/2005 | Michelson ............... 623/17.11 |

FOREIGN PATENT DOCUMENTS

SU     1 107 854     8/1984

* cited by examiner

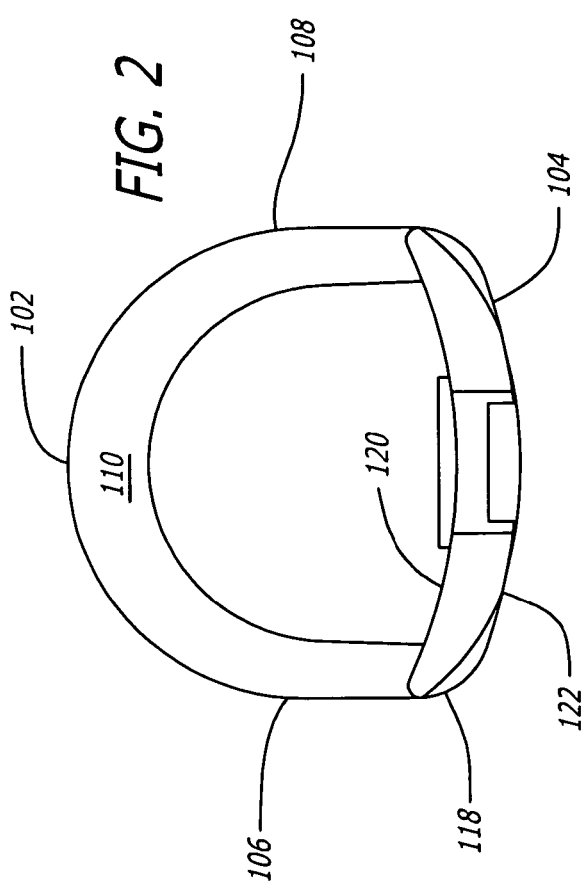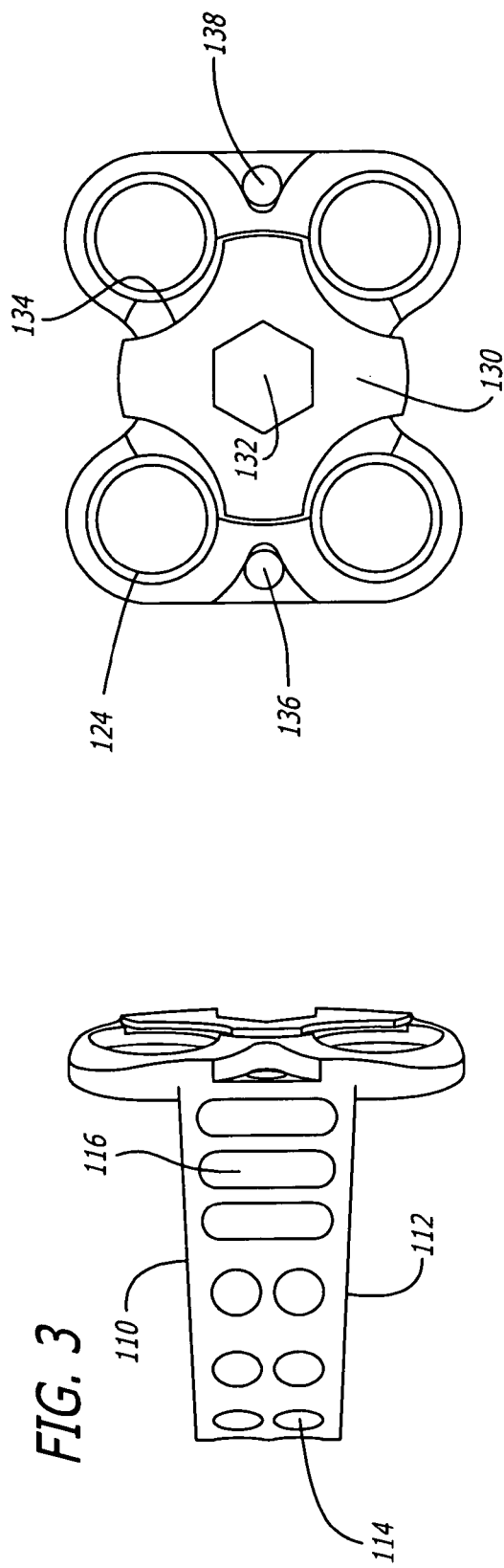

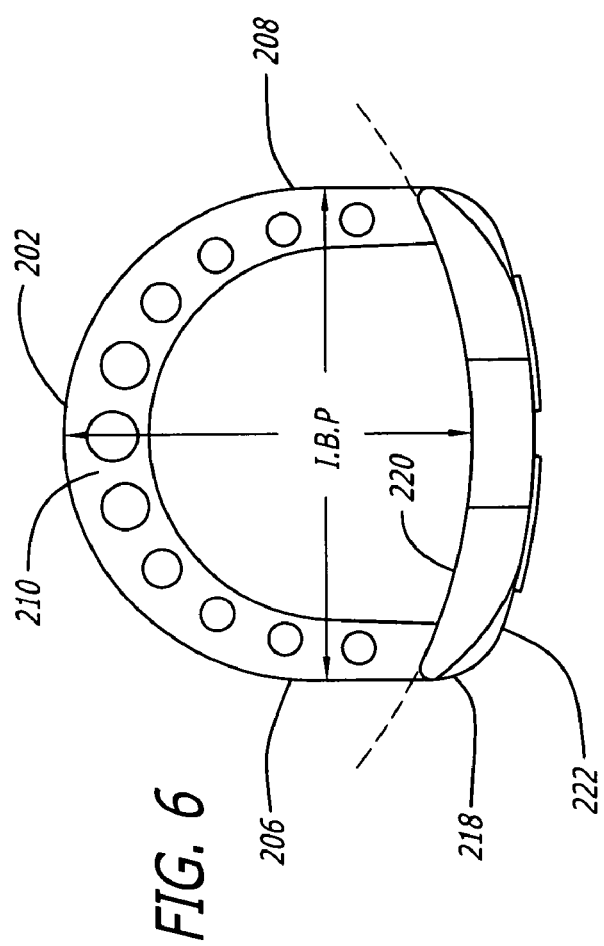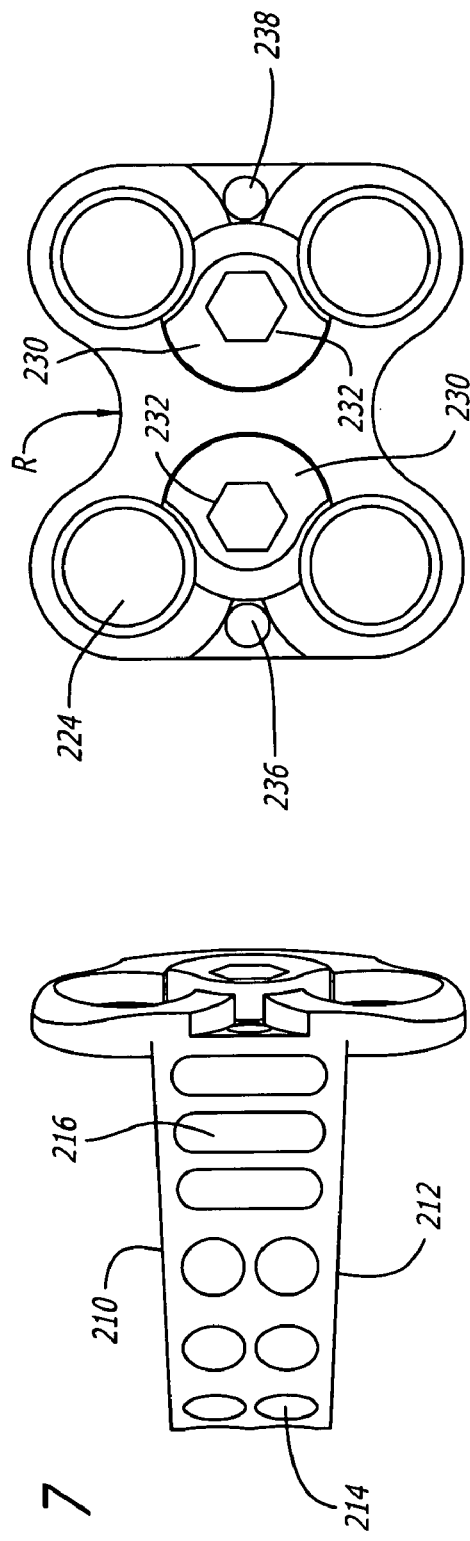

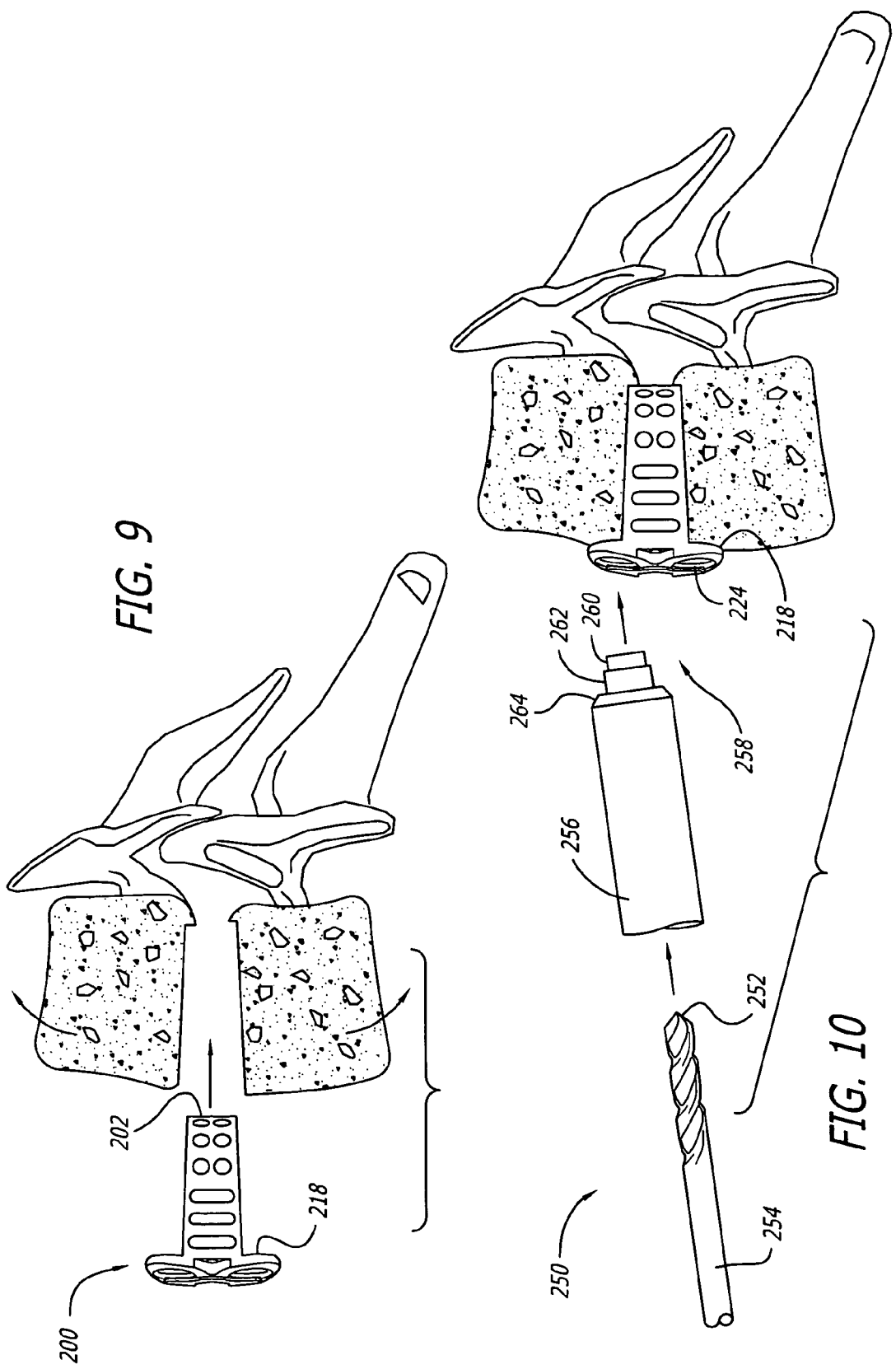

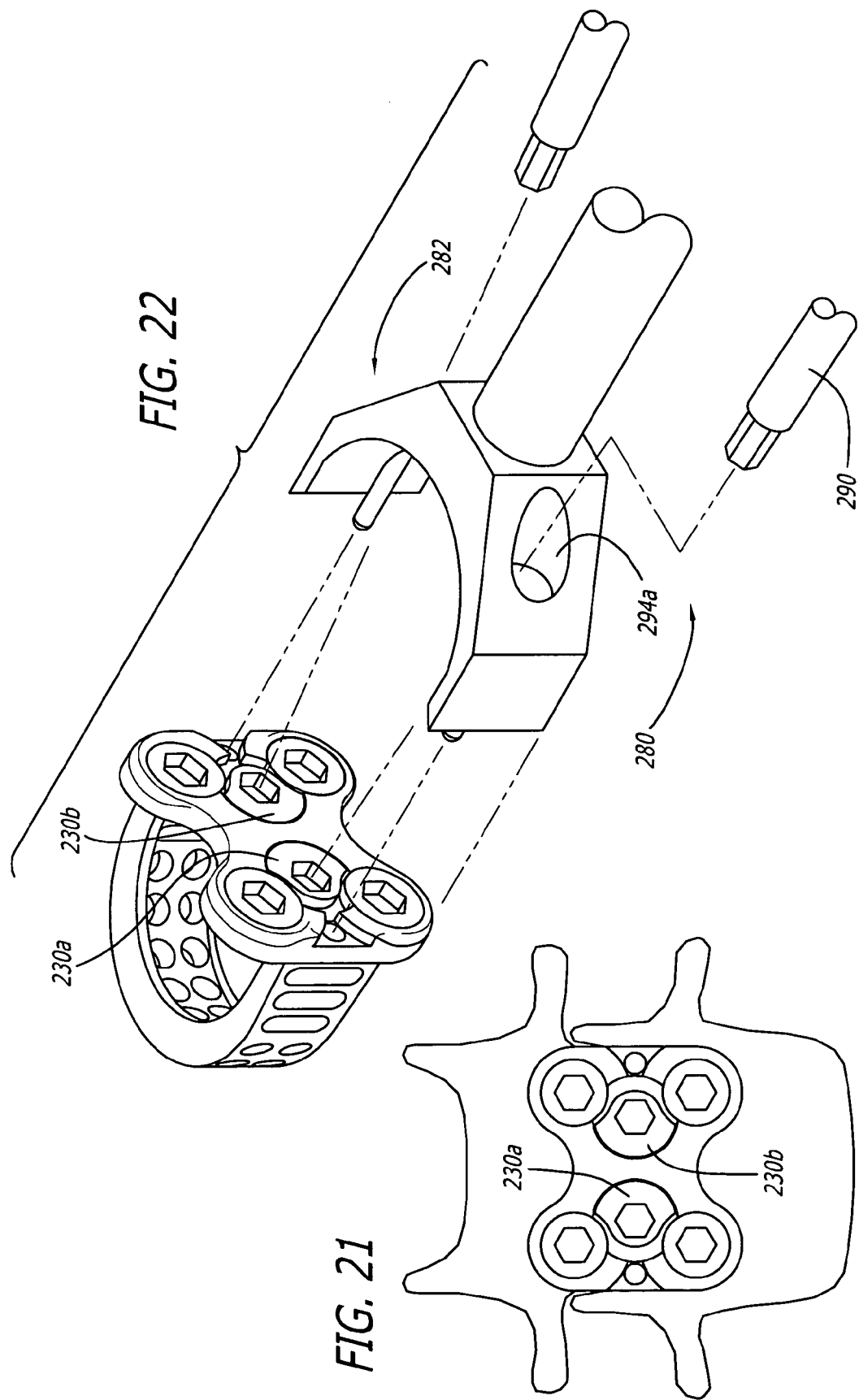

FLANGED INTERBODY SPINAL FUSION IMPLANTS

RELATED APPLICATION

This application is a continuation of U.S. application Ser. No. 09/903,141, filed Jul. 10, 2001 now U.S. Pat. No. 6,730,120; which claims benefit of U.S. Provisional Application No. 60/217,004, filed Jul. 10, 2000; all of which are incorporated by reference herein.

BACKGROUND

In the cervical spine, the average cervical disc is approximately 5–9 mm tall when healthy in an adult of normal stature. Presently, the screws for use in fixating into the cervical vertebral bodies are generally of a diameter of 4–5 mm each and have enlarged head portions for retaining them in the fixation device. Thus, these screws when placed in opposition and vertically aligned would have a combined height that exceeds the height of almost all cervical discs.

Implants of the related art have extended the height of the trailing end of the implant to make it taller than the disc space. An example of this is a flanged implant. The flanged implant makes it possible to place screws so that they can be vertically aligned and have sufficient structure of the implant to retain them. The flanged portion of the implant extends outside of the disc space.

In known interbody spinal fusion implants there have been problems with loosening and backing out of screws into the patient's throat area. These occurrences generally require further surgical procedures to replace the implants and screws entirely, and to repair any damage that may have been caused.

There is a need for an implant having a locking mechanism that can be easily and reliably locked in place to prevent the loosening of and backing out of the bone screws used to attach the implant to the vertebrae in the anterior aspect of the cervical, thoracic, and lumbar spine.

SUMMARY OF THE INVENTION

The present invention is directed to an interbody spinal fusion implant having an interbody portion for introduction into a disc space between adjacent vertebral bodies and a flanged portion that extends outside the disc space to overlie at least a portion of the anterior aspect of the vertebral bodies to be fused proximate that disc space. The flanged portion is configured to receive at least two opposed bone screws. The flanged portion includes at least one locking mechanism for locking the bone screws to the implant. At least one of the bone screws is directed into one of the adjacent vertebral bodies and at least another of the bone screws is directed into the other of the adjacent vertebral bodies for securing the implant to the adjacent vertebral bodies. The bone screws have a leading end, a shaft, threading upon the shaft, and a trailing end. The implant and the trailing end of the bone screw are adapted to cooperatively engage each other so as to prevent further advance of the bone screws through the implant. The flanged portion of the spinal implant of the present invention with the screws inserted is low profile so that the bone screw trailing ends do not substantially protrude from the flanged portion so as to not endanger the patient's overlying tissues, adjacent vessels, and neurological structures.

The bone screws are locked to the flanged portion by a locking mechanism so that the bone screws cannot get loose and/or migrate. The locking mechanism can be a single locking mechanism for locking only one screw to the flanged portion of the implant or a multilocking mechanism for locking two or more screws simultaneously to the flanged portion of the implant. For example, the multilocking mechanism can be a dual locking mechanism for locking two screws to the flanged portion of the implant or a locking mechanism for locking four bone screws to the flanged portion of the implant.

In the various embodiments of the present invention, the locking mechanisms and flanged portion may be configured to either rigidly capture the bone screws so that their positions are fixed, or alternatively allow for the screw angles to be variable in which case the screw angles may remain variable or be fixed when locked.

The flanged implants of the present invention may be configured so that the leading end is a portion of a circle; and where the depth of the implant is sufficient, the leading end is half of a circle; and where the depth of the implant is sufficient, the implant may have generally parallel side walls defining an implant width equal to the diameter of that circle.

In a preferred embodiment of the flanged implant of the present invention, the flanged portion has at least two bone screw receiving holes located at different distances from the mid-longitudinal axis of the implant. Such a configuration permits two such implants can be placed in successive levels of the spine without the bone screws of one implant interfering with the bone screws of the other.

A preferred method of the present invention for inserting a flanged implant at least in part between adjacent vertebral bodies adjacent a disc space and in part along the anterior aspects of the vertebral bodies includes preparing a recipient socket across the disc space and into the adjacent vertebral bodies and locking at least one of the bone screws to the implant.

Another preferred method of the present invention for inserting a flanged implant at least in part between adjacent vertebral bodies adjacent a disc space and in part along the anterior aspects of the vertebral bodies includes preparing a recipient socket across the disc space and into the adjacent vertebral bodies wherein the socket corresponds in shape to the shape of the interbody portion of the flange implant.

Although a preferred embodiment of the present invention has been shown for use in the cervical spine, the flanged implants of the present invention may be used in the thoracic and lumbar spine from the anterior aspects. While the above-described configurations are preferred for various advantages, they do not in any way limit the breadth of the present invention which is limited only by the claims.

BRIEF DESCRIPTION OF THE DRAWINGS

FIG. 2 is a top plan view of the flanged spinal implant of FIG. 1.

FIG. 3 is a side elevation view of the flanged spinal implant of FIG. 1.

FIG. 4 is a trailing end elevation view of the flanged spinal implant of FIG. 1.

FIG. 6 is a top plan view of the flanged spinal implant of FIG. 5.

FIG. 7 is a side elevation view of the flanged spinal implant of FIG. 5.

FIG. 8 is a trailing end elevation view of the flanged spinal implant of FIG. 5.

FIG. 9 is a side elevation view of an embodiment of the flanged spinal implant of the present invention shown being inserted into an implantation space formed across the disc space between two adjacent vertebral bodies of the spine shown in partial cross-section.

FIG. 10 is a side elevation view of a drill and drill guide for forming bone screw receiving holes into adjacent vertebral bodies corresponding to bone screw receiving openings in the trailing end of the flanged spinal implant of the present invention implanted between two adjacent vertebral bodies shown in partial cross-section.

FIG. 21 is a trailing end elevation view of the flanged spinal implant of FIGS. 5–8, having two locking mechanisms, installed between two adjacent vertebral bodies shown in the unlocked position.

FIG. 22 is an exploded view of the flanged spinal implant of FIG. 21 and driver holder instrument and locking tool for installing and locking the implant.

DETAILED DESCRIPTION OF THE DRAWINGS

Figure 1:
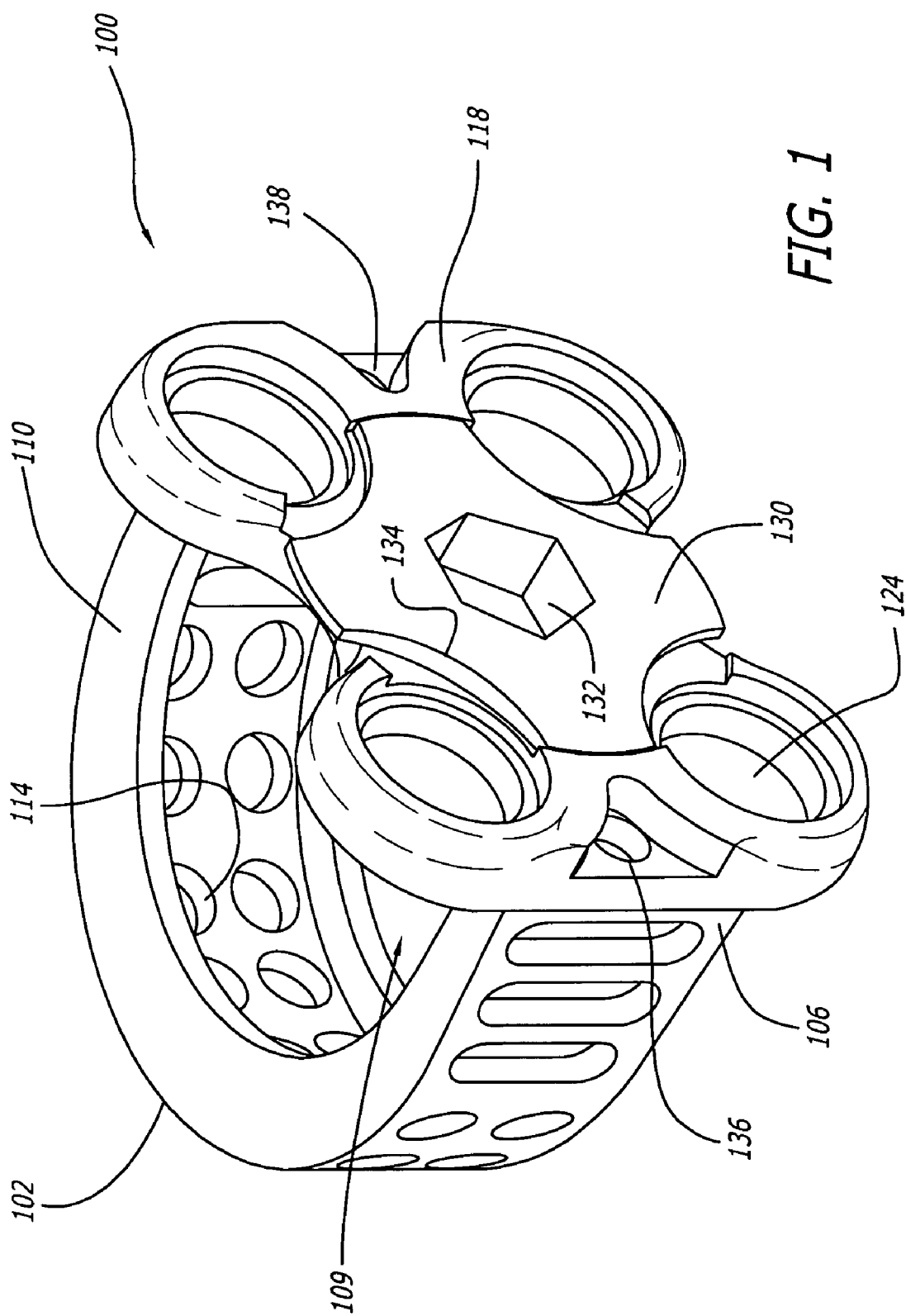
FIG. 1 is a trailing end perspective view of a first embodiment of the flanged spinal implant of the present invention.
Figure 5:
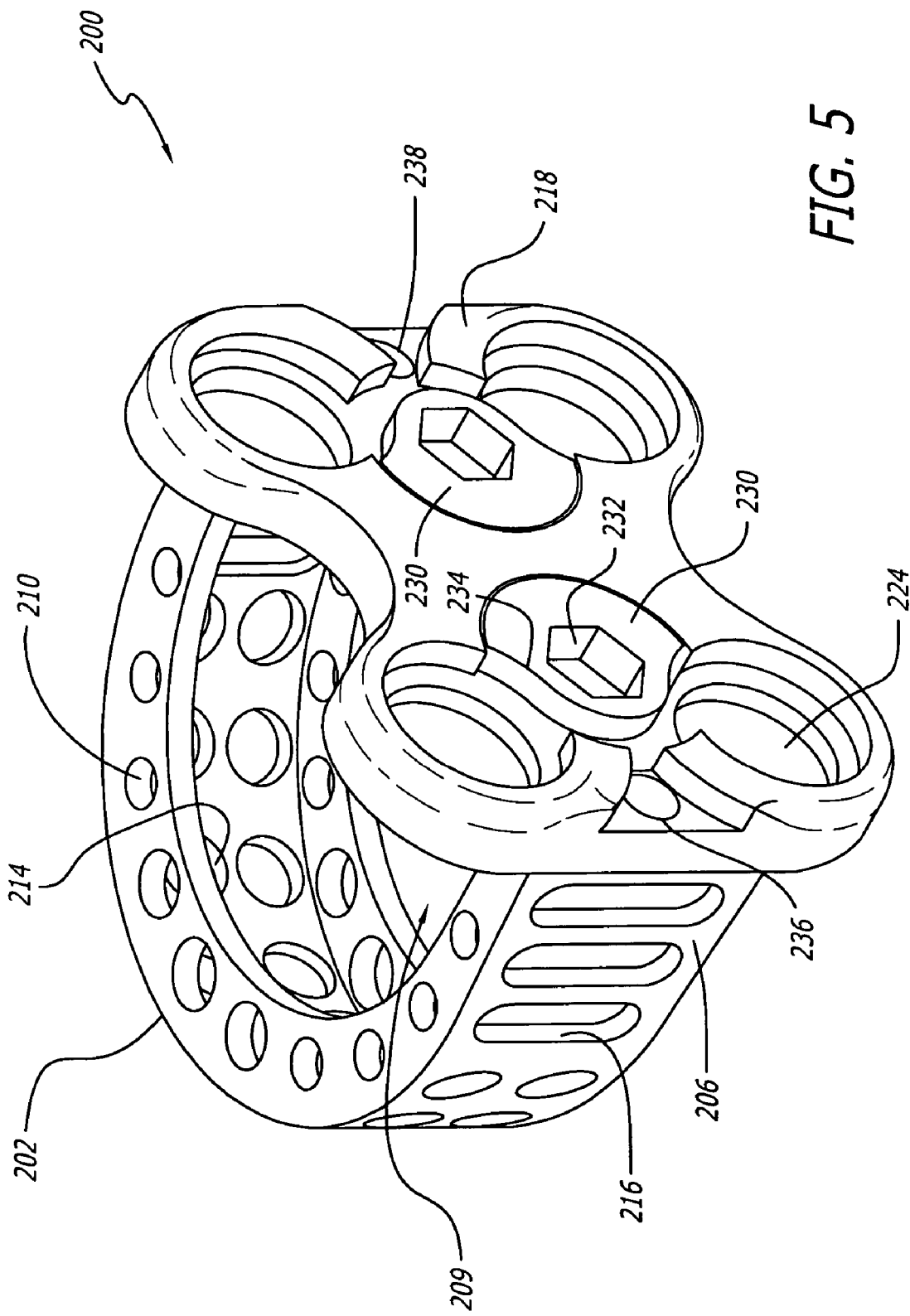
FIG. 5 is a trailing end perspective view of a second embodiment of the flanged spinal implant of the present invention.

Reference will now be made in detail to the present preferred embodiments of this invention, examples of which are illustrated in the accompanying drawings. Similar reference numbers such as "102, 202" will be used throughout the drawings to refer to similar portions of different embodiments of the present invention.

As shown in FIGS. 1–4, a first embodiment of the spinal implant of the present invention is generally referred to by the numeral 100. As used herein, the term "implant" includes any interbody spinal fusion implant regardless of the material from which it is formed, including specifically surgical quality metal, plastics, ceramics, cortical bone, and other material useful for the intended purpose, including materials that may be in whole or in part bioresorbable. Implant 100 has a leading end 102, an opposite trailing end 104, and sides 106 and 108 therebetween for connecting, spanning, or joining, ends 106, 108.

In a preferred embodiment, leading end 102 can be a portion of a circle and where the depth of the implant is sufficient, leading end 102 is a portion of a circle. The implant width can be equal to that portion of the circle, or if a half circle, then the diameter of that circle. Alternatively, leading end 102 may be straight at least in part, and for example the straight part can be at an approximately right angle to sides 106, 108 to form a generally rectangular or square shape for example. The configuration of the leading end of the implant of the present invention may be adapted to match the configuration of an implantation space formed across the disc space and into the adjacent vertebral bodies in accordance with applicant's U.S. Pat. No. 6,159,214 titled "Milling Instrumentation and Method for Preparing a Space Between Adjacent Vertebral Bodies" and U.S. Pat. No. 6,224,607 titled "Instrument and Method for Creating an Intervertebral Space for Receiving an Implant," both of which are incorporated by reference herein. Implant 100 has a vertebral body engaging upper surface 110 and an opposite vertebral body engaging lower surface 112. Upper and lower surfaces 110, 112 may have at least one opening and may have a plurality of openings therethrough for permitting the growth of bone from adjacent vertebral body to adjacent vertebral body through implant 100. By way of example, the upper and lower surfaces of the implant may be convergent toward one another from trailing end to leading such that the implant is able to place the adjacent vertebral bodies in angular relationship to each other such as to produce lordosis by example.

Both ends 102 and 104 may include openings such as 114 so as to permit for the growth of bone and vascular access therethrough. Similarly, sides 106, 108 can include openings such as 116 for similar or other purposes. Implant 100 preferably has an open interior 109 between sides 106, 108 to permit for the growth of bone from adjacent vertebral body to adjacent vertebral body through open interior portion 109. The implant 100 itself, any of its various surfaces, open interior 109 and/or any of its openings such as 114, 116, for example, can be coated with, or contain bone growth promoting materials, including but not limited to, bone, bone morphogenetic proteins, hydroxyapatite, genes coding for the production of bone, or any other material that intrinsically participates in the growth of bone from one of the adjacent vertebral bodies to the other of the adjacent vertebral bodies at the fusion site.

Trailing end 104 is configured into a flanged portion 118 having an interior surface 120 and an exterior surface 122. Interior surface 120 is adapted to contact the anterior aspect of the adjacent vertebral bodies. In a preferred embodiment, interior surface 120 may be curved to conform to at least a portion of the natural curvature of the anterior aspect of the vertebral bodies. For example, interior surface 120 may be concave in a horizontal plane, in a vertical plane, or biconcave in both the vertical and horizontal planes. Exterior surface 122 may, but need not, correspond to the configuration of interior surface 120. In the preferred embodiment, exterior surface 122 is configured to eliminate sharp edges and corners to prevent damage to the adjacent delicate vascular and neural structures within the body. For example, exterior surface 122 can be tapered at its exterior edges and can have rounded corners. The spinal implant may also have a generally anatomic trailing end that conforms to the peripheral contours of the adjacent vertebral bodies or that approximates a portion of a circle having an arc of radius greater than that of the implant leading end.

Flanged portion 118 includes bone screw receiving holes 124 for receiving bone screws 170 for securing implant 100 to the adjacent vertebral bodies. The flanged portions of the implant may be configured to receive bone screws in whole or in part, such that they are constrained within the bone screw receiving holes (i.e., fixing the trajectory of each bone screw), or left unconstrained within the bone screw receiving holes for allowing variable screw angles.

Flanged portion 118 includes a locking mechanism 130 for locking the bone screws to implant 100. Locking mechanism 130 can be in the form of a screw or a rivet having a head for contacting and securing the bone screws to implant 100. Locking mechanism 120 is adapted for rotational movement relative to flanged portion 118. Locking mechanism 130 includes a tool-engaging portion 132 for moving locking mechanism 130 from an unlocked to a locked position. Locking mechanism 130 further includes relieved portions 134 permitting the installation of bone screws into bone screw receiving holes 124 while locking mechanism 130 is in the unlocked position. In a preferred embodiment, in the open position locking mechanism 130 is 45 degrees short of being fully tight if mechanism 130 is a screw, or if as shown as a rivet 45 degrees rotated from the locked position. The bottom of the head of locking mechanism 130 can be of various shapes and, for example, can be ramped or concave. Various embodiments of the locking mechanisms are adapted to lock one bone screw only, or at least two bone screws and either of the locking elements may be pre-installed to the implant. Pre-installation of the locking mechanisms by the manufacturer prior to the insertion of the bone screws by the physician facilitates the procedure in that the physician does not have to attach the locking mechanism to the plate as a separate procedure during the operation.

In the various embodiments of the present invention, locking mechanisms 130 and flanged portion 118 may be configured to either rigidly capture bone screws so that their positions are fixed, or alternatively allow for the screw angles to be variable in an unconstrained state in which case the screw angles may remain variable when locked. Locking mechanism 130 can work either to constrain the bone screws by fixing their positions, or in the alternative by preventing the bone screws from backing out without fixing the screws position so that the screws can allow for settling of the disc space (dynamization), which may be desirable. If it is desired to have the bone screws constrained in the bone screw receiving holes, a locking mechanism can be used to bind at least a portion of the bone screw in the locked position. Preferably, for a constrained configuration an interference fit is formed between the wall of the bone screw receiving hole and the trailing end or head of the screw to prevent the screws from moving within the bone screw receiving hole.

If it is desired to have the bone screws unconstrained in the bone screw receiving holes, a locking mechanism can be used to bind the flanged portion directly such that the bone screws may be permitted to move relative to the flanged portion while being prevented from backing out of the bone screw hole by the locking mechanism. In the unconstrained configuration, the bone screws may have a rounded head portion and/or a reduced neck diameter to permit movement of the bone screws so as to allow the angle between the implant and the bone screw to be variable.

Flanged portion 118 further includes alignment holes 136 and 138 for engaging alignment pegs 190 from a driver instrumentation described below.

A preferred origin and trajectory of bone screw receiving hole 124 is such that a surgeon can (but does not necessarily have to) be able to insert bone screws through holes 124 to an optimal or desired depth without those bone screws crossing a plane bisecting the height of the adjacent vertebral body. An alternative embodiment may include top and bottom screws that are placed asymmetrically so as to be offset from one another so that the screws from such implants inserted into adjacent disc spaces pass each other in an intermediate vertebral body without hitting one another. For example, an implant may have two bone screws in the flanged portion toward the outer sides and projecting through the upper surface and one bone screw in the middle of the trailing end projecting through the lower surface. Further, an implant may have a pair of bone screws in one of the upper or lower portions of the flanged portion that are spaced apart more narrowly than a pair of screws in the opposite one of the upper or lower portions of the flanged portion. Two such implants can be placed in successive levels of the spine without the bone screws of one implant interfering with the bone screws of the other. Alternatively, the bone screws are preferably placed adequately close together and preferably penetrate into a portion of the vertebral body closest to the disc space into which the implant is being installed so as not to interfere with bone screws from a second implant being installed in an adjacent disc space where consecutive levels of the spine are being fused.

The flanged portion of any of the embodiments described herein is preferably configured to permit access to the vertebral bodies by instrumentation for positioning the vertebral bodies relative to each other. For example, the flanged portion as shown in the drawings is configured to permit the placement of a pin or leg of an instrument into engagement with the bone of the vertebral bodies above and below the flanged portion and at least in part between the bone screw receiving holes in order to compress or distract the disc space. As an example, the flanged portion may have a reduced dimension (indicated by the reference letter R in FIG. 8) between the sides of the trailing end, a slot, or a notch to permit the placement of a positioning instrument proximate to the flanged portion at least in part between the bone screw receiving holes (but not necessarily within the flanged portion itself) and into the bone of the vertebral bodies. Such a configuration of the flanged portion is especially beneficial when two consecutive levels of the spine are being fused with two flanged spinal fusion implants of the present invention. The configuration of the flanged portion of the spinal implant of the present invention further permits greater exposure of the vertebral bodies to allow for more vascular growth than related art flanged implants. The flanged portion of the spinal implant of the present invention is more compact than plates of spinal fixation devices of the related art, and the use of an interbody spinal fusion implant of the related art and a typical anterior cervical plate, wherein the bone screw receiving openings would be spaced further apart.

As shown in FIGS. 5–11, a second embodiment of a spinal implant in accordance with the present invention is shown and generally referred to by the reference numeral 200. Implant 200 is similar to implant 100, except that flanged portion 218 includes two locking mechanisms 230, each locking two bone screws to spinal implant 200. Locking mechanisms 230 are preferably positioned each in a recess formed in flanged portion 218 and are configured to permit the insertion of bone screws into bone screw receiving holes 224 while locking mechanisms 230 are in the unlocked position. In a preferred embodiment, locking mechanisms 230 can turn 180 degrees to be fully tightened. Locking mechanisms 230 can both turn clockwise or one counter to the other.

As shown in FIG. 9, implant 200 is inserted into an implantation space formed across the disc space into the adjacent vertebral bodies. As an example, the implantation space can be prepared with the methods and instrumentations disclosed in applicant's U.S. Pat. No. 6,159,214, titled Milling Instrumentation and Method for Preparing a Space Between Adjacent Vertebral Bodies and U.S. Pat. No. 6,224,607, titled Instrument And Method For Creating An Intervertebral Space For Receiving An Implant, both of which are identified above and incorporated by reference herein. Implant 200 is installed with leading end 202 inserted first into the disc space and flanged portion 218 contacts the anterior aspect of the vertebral bodies.

As shown in FIG. 10, bone screw receiving openings may be formed into the adjacent vertebral bodies with a drill 250 and a drill guide 256. Drill 250 can be any of well-known bone removal devices and can have a bone removing end 252 and a shaft 254. Drill guide 256 has a leading end 258 adapted to be inserted into one of bone screw receiving holes 224 of flanged portion 218. Leading end 258 has a smaller dimension 260, a larger dimension 262, and a shoulder 264 corresponding to the reduced dimension portions of bone screw receiving holes 224 that are configured to receive the head portion of bone screws 270. Drill guide 256 has an inner bore 266 that in one embodiment is aligned with the central longitudinal axis of the bone screw receiving holes 224 when leading end 258 is properly seated therein. If it is desired to vary the angle of drill guide 256 to bone screw receiving hole 126, the tip of drill guide 256 may be rounded. In the alternative, the drill guide may screw into the bone screw receiving hole, or may attach to the implant by any other technique known in the art. Further, the openings into the bone may be formed with a spike or other means, or the screws may be inserted without first forming bores into the bone.

Figure 11:
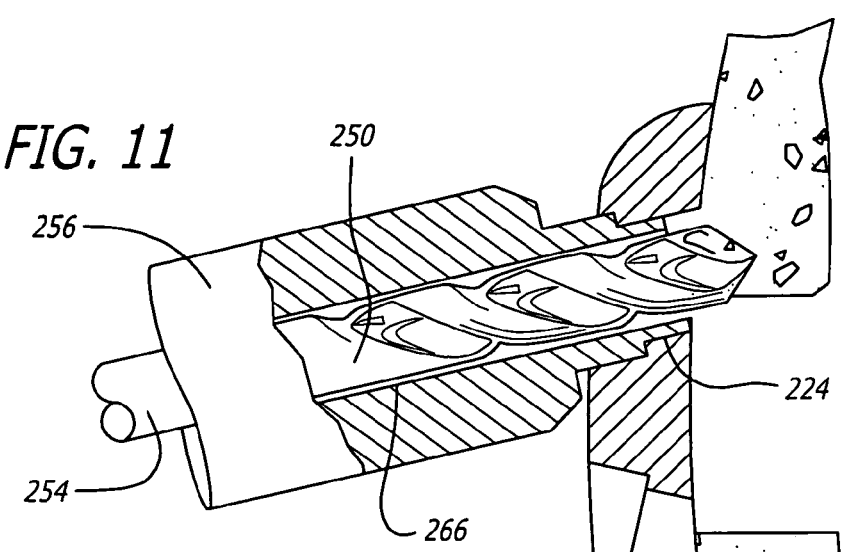
FIG. 11 is an enlarged fragmentary view of a drill guide and flanged portion of the spinal implant shown in partial cross-section with a drill passing therethrough to form a bone screw receiving opening into one of the adjacent vertebral bodies shown in partial cross-section.

As shown in FIG. 11, when drill guide 256 is seated within bone screw receiving hole 224, drill 250 passes through inner bore 266 to form a bone screw receiving opening into the bone of the adjacent vertebral bodies corresponding to bone screw receiving holes 224. In the preferred embodiment, bone screw receiving openings are formed in the bone located at or proximate the junction of the two cortices of the vertebral bodies.

Figure 12:
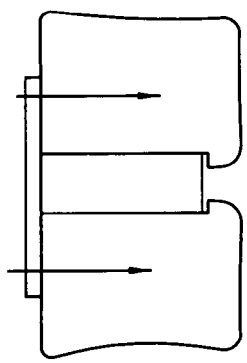
FIG. 12 is a side elevation view of a prior art spinal implant and plate combination inserted into a disc space between two adjacent vertebral bodies with the orientation of the bone screws relative to each other, the plate, and vertebral bodies illustrated by the two arrows.

As shown in FIG. 12, spinal fixation devices of the related art provided for the bone screws to be oriented in the parallel position to each other and distanced away from the disc space.

Figure 13:
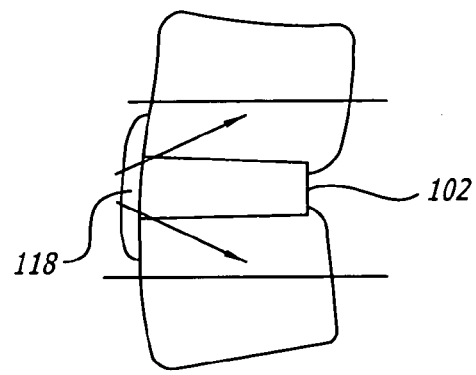
FIG. 13 is a side elevation view of an embodiment of the flanged spinal implant of the present invention inserted into the disc space between adjacent vertebral bodies with the orientation of the bone screws relative to each other, the flanged portion, and vertebral bodies illustrated by the two arrows.
Figure 14A:
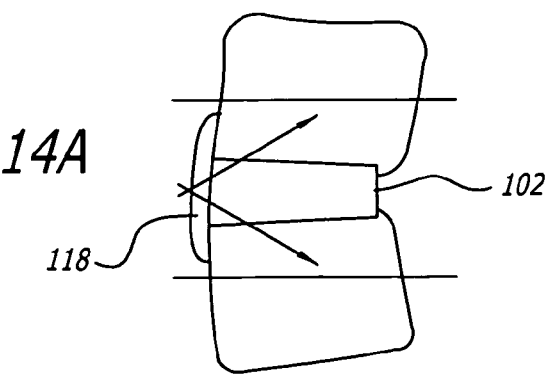
FIG. 14A is a side elevation view of an embodiment of the flanged spinal implant of the present invention inserted into the disc space between two adjacent vertebral bodies with the orientation of bone screws relative to each other, the flanged portion and vertebral bodies illustrated by the two arrows.
Figure 14B:
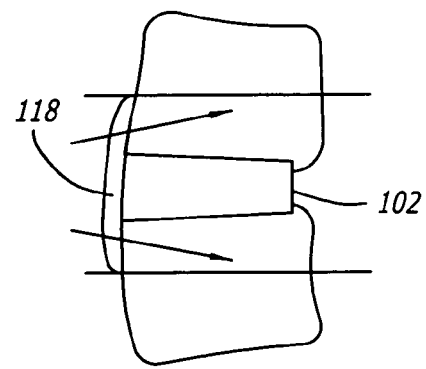
FIG. 14B is a side elevation view of an alternative embodiment of the flanged spinal implant of the present invention inserted into the disc space between two adjacent vertebral bodies with the orientation of bone screws relative to each other, the flanged portion and vertebral bodies.

As shown in FIGS. 13–14B, in the flanged spinal implant of the present invention, the bone screws can be oriented in an angular relationship to each other, to the flanged portion, and to the upper and lower surfaces of the implant. The bone screws may be divergent along the vertical plane of the implant when installed into the adjacent vertebral bodies. The preferred angular divergence from the implant surface is preferably 25°–40°, but any angle useful for the intended purpose is within the scope of the present invention. In a preferred embodiment, screws are angled such that they do not extend beyond half the height of the adjacent vertebral body. This ensures that screws of one implant will not contact the screws of an implant inserted in a neighboring disc space.

For example, first, one of bone screws 170 can be inserted through flanged portion 118 at an angle to the flanged portion and then another bone screw can be inserted sliding by first bone screw. In the implant of the present invention, if lag screws are utilized or if there is a lagging implant to screw relationship, then the adjacent vertebral bodies are pulled toward implant 100 as bone screws 100 are installed into the vertebral bone to create a compressive load on the implant. Further, the angling of bone screws 170, keeps the anterior portion of the adjacent vertebral bodies together during extension movement of the spine such as would occur when a patient leans backwards. Among the many advantages of the present invention, the anterior portions of the vertebral bodies adjacent implant 100 do not move apart as they are held in place by bone screws 170 inserted through flanged portion 118, the back of the implant is not driven into the vertebral bodies with spinal extension, and healthy compressive load is safely distributed over the entire length of the interbody portion of the implant.

As shown in FIG. 14A, in an embodiment of the present invention, from an insertion point on flanged portion 118 corresponding to a position inside the disc space, first one bone screw can be inserted through flanged portion 118 at an angle to the flanged portion and then another bone screw can be inserted sliding by the first bone screw as illustrated by the arrows.

As shown in FIG. 14B, in another embodiment of the present inventions, from a point on flanged portion 118 corresponding to a position outside of the disc space, bone screws may be inserted at an angle to the implant into the adjacent vertebral bodies as illustrated by the arrows.

Figure 15:
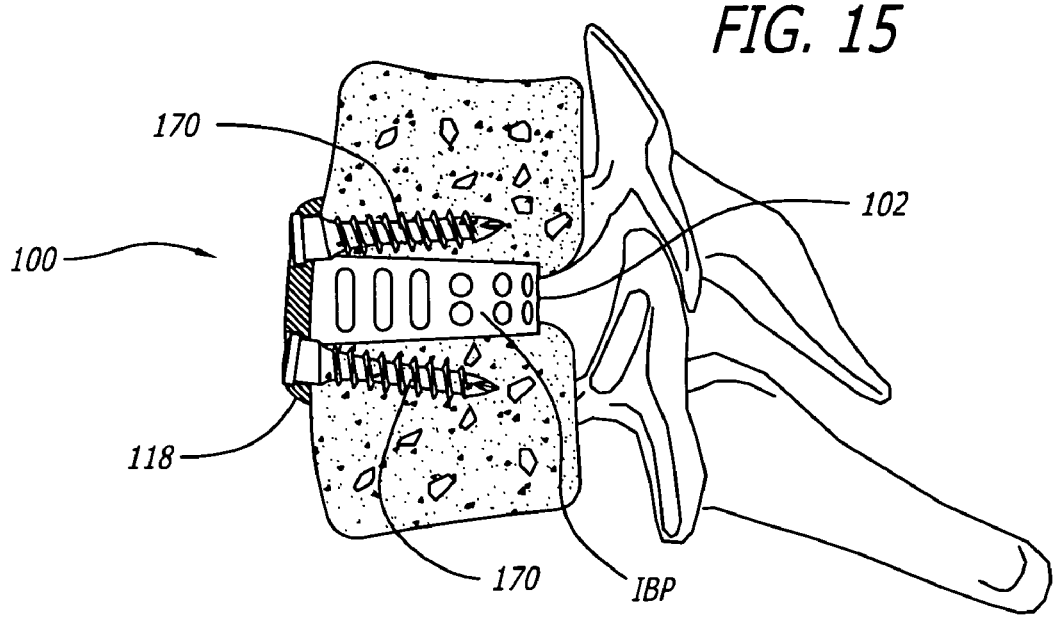
FIG. 15 is a side elevation view of an embodiment of the flanged spinal implant of the present invention as per FIG. 13 shown in partial cross-section inserted between two adjacent vertebral bodies shown in partial cross-section with bone screws installed.

FIG. 15 shows implant 100 installed with leading end 102 inserted first such that an interbody portion IBP is within the disc space between two adjacent vertebral bodies and flanged portion 118 is against the anterior aspect of the vertebral bodies. Bone screws 170 are installed through bone screw receiving holes 224 and into the bone of the adjacent vertebral bodies.

Figure 16:
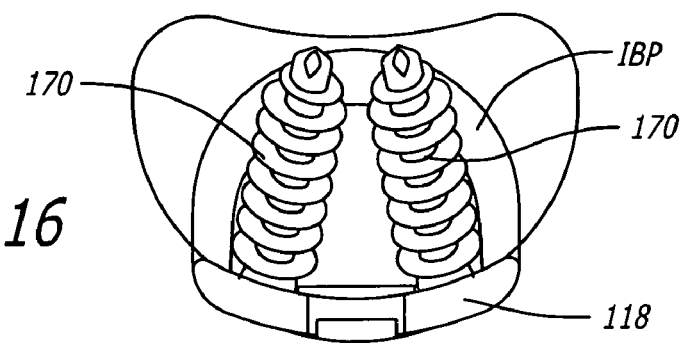
FIG. 16 is a top plan view of the flanged spinal implant of FIGS. 1–4 in the inserted position with one of the adjacent vertebral bodies shown.

FIG. 16 shows a top plan view of implant 100 installed with interbody portion within the disc space between two adjacent vertebral bodies and bone screws 170 installed through flanged portion 118. In a preferred embodiment, bone screws 170 are toed-in toward each other as shown in FIG. 16. It is appreciated, however, that bone screws 170 may be oriented in various positions relative to one another.

Figure 17:
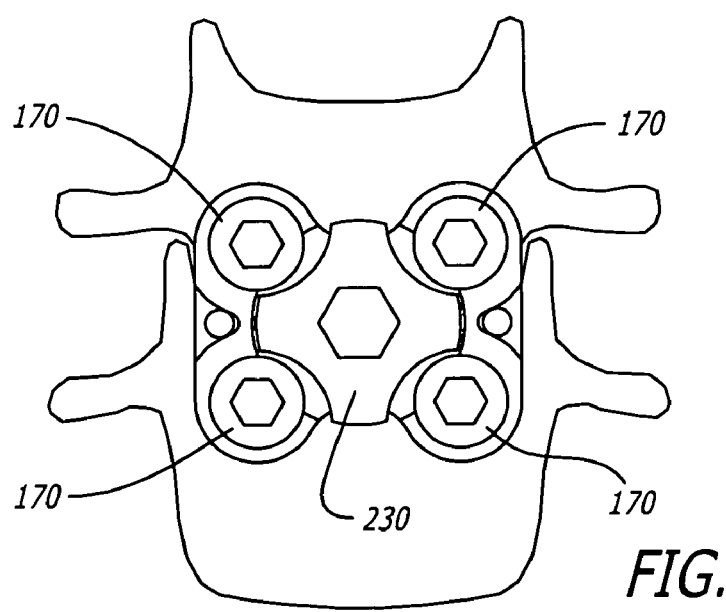
FIG. 17 is a trailing end elevation view of the flanged spinal implant of FIGS. 1–4 and the adjacent vertebral bodies into which it is installed.

As shown in FIG. 17, four bone screws 170 can be installed through the flanged portion 118 with the locking mechanism 130 in the unlocked position. Locking mechanism 130 can be rotated to lock bone screws 170 to the flanged portion 118 to prevent unwanted backing out of the bone screws 170.

Figure 18:
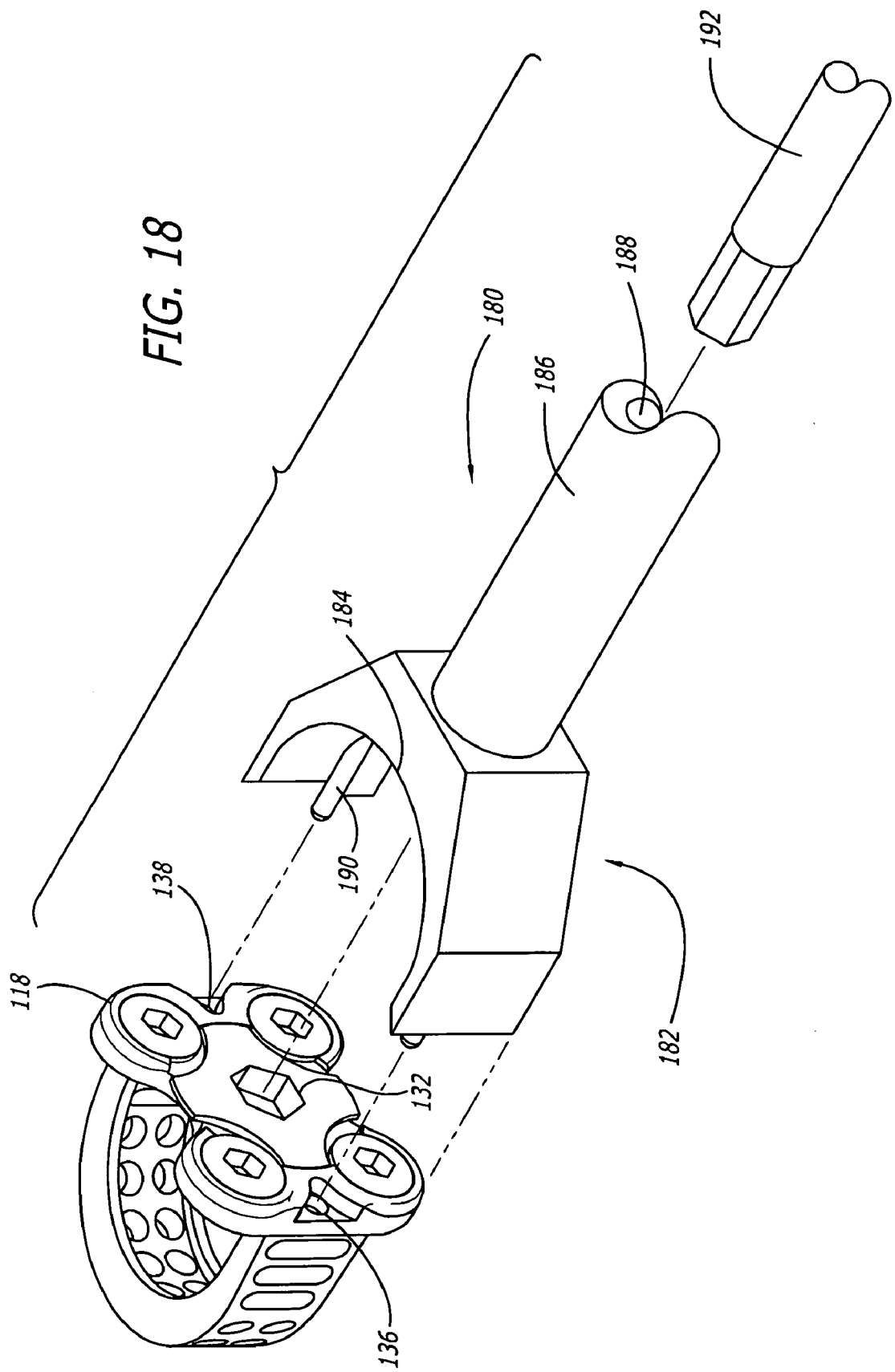
FIG. 18 is an exploded side perspective view of the embodiment of the flanged spinal implant of FIGS. 1–4, a driver and implant holder instrument, and a locking tool instrument for installing and locking the implant.

As shown in FIG. 18, implant 100 can be installed with driver instrumentation 180 for both holding the implant so as to be useful for insertion and for preventing torquing of the implant when the locks are secured in their locked position. Driver instrumentation 180 has a blocker portion 182 for cooperatively engaging flanged portion 118 of implant 100. Blocker 182 has a leading arcuate surface 184 configured in a preferred embodiment to conform at least in part to the contour of flanged portion 118. Driver instrumentation 180 has a shaft 186 extending from blocker 182 with an inner bore 188 along the longitudinal axis of shaft 186. Extending from blocker 182 are a pair of alignment pegs 190 for cooperatively engaging alignment holes 136, 138 in flanged portion 118. Alignment pegs 190 in combination with alignment holes 136, 138 function to align driver instrumentation 180 with implant 100 such that inner bore 188 is aligned with locking mechanism 130. In this manner, a locking tool 192 for cooperatively engaging tool engaging portion 132 of locking mechanism 130 can be passed through inner bore 188 and access locking mechanism 130 to operate locking mechanism 130. Instrumentation 180 allows the surgeon to tighten locking mechanisms 130 against the blocker 182 instead of torquing the spine of the patient.

Driver instrument 180 and blocker 182 are shown as an example of insertion instrumentation with the understanding that any inserter or a blocker or combined inserter and blocker as would be known to one of ordinary skill in the art and useful for the intended purpose would be within the scope of the present invention.

Figure 19:
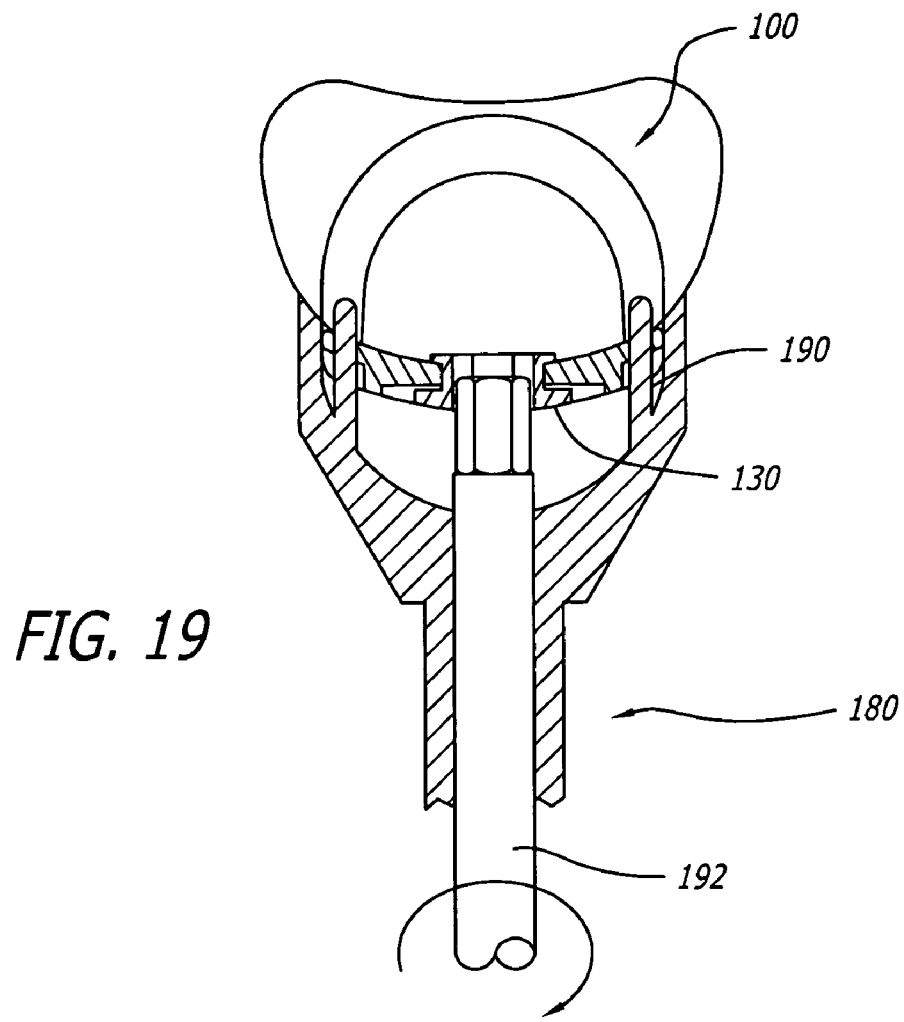
FIG. 19 is a top plan view in partial cross-section of the flanged spinal implant of FIGS. 1–4 installed between two adjacent vertebral bodies and the driver holder instrument and locking tool shown locking the locking mechanism of the implant.

FIG. 19 shows a top plan view in partial cross-section of flanged spinal implant 100 installed between two adjacent vertebral bodies and coupled to the driver/blocker instrument 180 with tool 192 (such as a screw driver for example) shown locking the locking mechanism 130 (a rivet for example) to secure bone screws 170 to flanged portion 118. It is appreciated that locking mechanism 130 could be a rivet, screw, cap, cover, or other.

Figure 20:
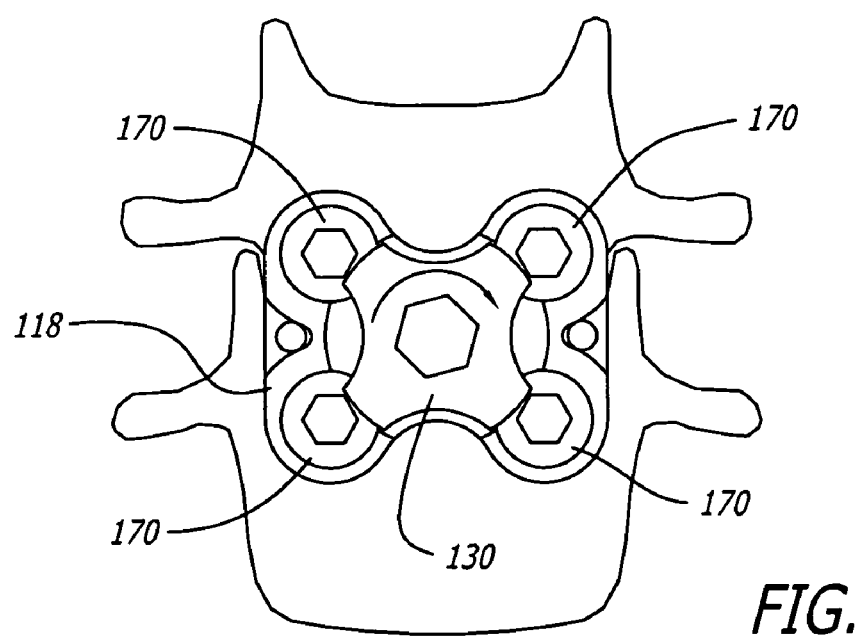
FIG. 20 is a trailing end elevation view of the flanged spinal implant of FIGS. 1–4 installed between two adjacent vertebral bodies with the locking mechanism in the locked position locking four bone screws.

FIG. 20 shows locking mechanism 130 rotated to the locked position in the direction of the arrow to lock bone screws 170 to flanged portion 118.

FIG. 21 is a trailing end elevation view of flanged spinal implant 200 installed between two adjacent vertebral bodies with locking mechanisms 230a and 230b shown in the unlocked position and bone screws 270 in place.

FIG. 22 shows driver/blocker instrument 280 for installing implant 200 and for locking the locking mechanisms 230a and 230b. Driver instrument 280 has driver/blocker 282 configured to cooperatively engage flanged portion 218 of implant 200. Blocker 282 has openings 294a and 294b that are coaxially aligned with locking mechanisms 230a and 230b, respectively. Openings 294a and 294b are configured to receive a locking tool 292 therethrough for accessing and operating locking mechanisms 230a and 230b.

Figure 23:
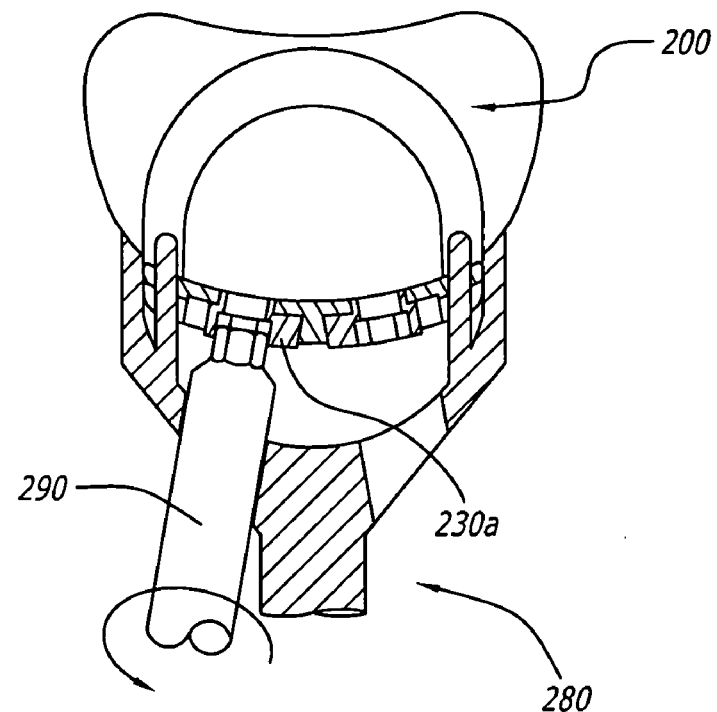
FIG. 23 is a top plan view in partial cross-section of the spinal implant of FIG. 21 installed between two adjacent vertebral bodies with the driver holder instrument and locking tool locking one of the locking mechanisms of the implant in the inserted position with one of the adjacent vertebral bodies shown.

FIG. 23 shows a top plan view in partial cross-section of flanged spinal implant 200 installed between two adjacent vertebral bodies and coupled to driver/blocker instrument 280 with tool 292 (such as a screw driver for example) shown locking the locking mechanism 230a to secure bone screws 270 to flanged portion 218.

Figure 24:
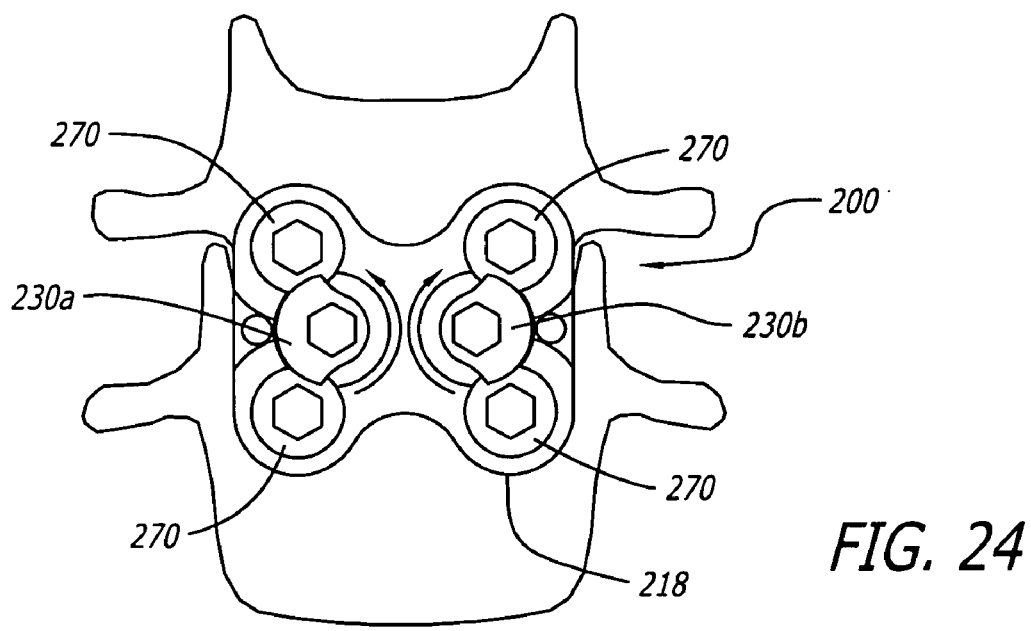
FIG. 24 is a trailing end elevation view of the spinal implant of FIG. 21 with the locking mechanisms shown locking all four bone screws to the implant.

FIG. 24 is a trailing end elevation view of flanged spinal implant 200 installed between two adjacent vertebral bodies with locking mechanisms 230a and 230b shown in the locked position in the direction of the arrow to lock bone screws 270 to flanged portion 218.

Figure 25:
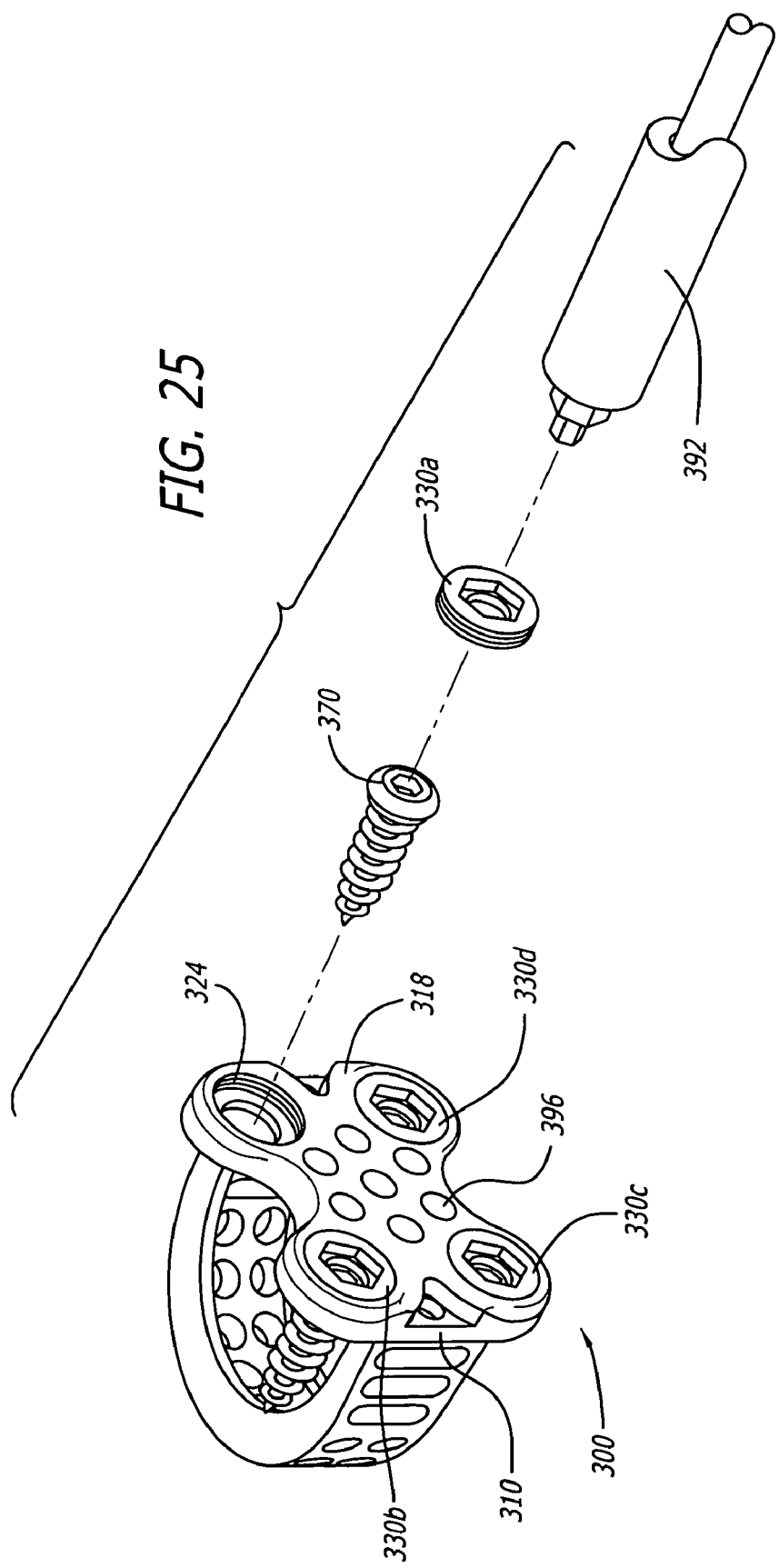
FIG. 25 is a trailing end perspective view of a third embodiment of the flanged spinal implant of the present invention shown with a bone screw, locking mechanism, and two-stage installation instrument for both inserting the bone screws and locking them to the implant.

As shown in FIG. 25, a third embodiment of the spinal implant of the present invention is shown and generally referred to by the reference numeral 300. Implant 300 may be similar to implant 200, except that flanged portion 318 does not include a multi-locking mechanism. Instead, implant 300 has single lock locking mechanisms 330a–d that coaxially engage bone screw receiving holes 324 to individually lock each of bone screws 370 to spinal implant 300. Flanged portion 310 further includes bone throughgrowth or vascular access holes 396 to allow for the growth of bone and vascularity through implant 300. A dual stage locking tool 392 (such as a screw driver) is used to install bone screws 370 and to install locking mechanism 330 to lock bone screw 370 to the flanged portion 318 with locking mechanism 330. This two stage driver is capable of carrying both the bone screw and the screw lock simultaneously. Driver instrumentation to lock the bone screws to implant 300 may, but need not, be used as locking mechanisms 330 require less torque than locking mechanisms 130 and 230 described herein It is appreciated that all the bone screws described herein may be self-tapping and may have a rigid fit into the flanged portion of the spinal implant so that they may be free to wiggle.

The spinal fusion implant of the present invention may include, be made of, treated, coated, filled, used in combination with, or contain artificial or naturally occurring materials suitable for implantation in the human spine. These materials include any source of osteogenesis, bone growth-promoting materials, bone derived substances, bone morphogenetic proteins, hydroxyapatite, genes coding for the production of bone, and bone including, but not limited to, cortical bone. The implant can also be formed of material such as metal including, but not limited to, titanium and its alloys, surgical grade plastics, plastic composites, ceramics, or other materials suitable for use as a spinal fusion implant. The implant can include at least in part materials that are bioabsorbable in the body. The implant of the present invention can be formed of a porous material or can be formed of a material that intrinsically participates in the growth of bone from one of adjacent vertebral bodies to the other of adjacent vertebral bodies. The implant may be treated with, coated with, or used in combination with substances to inhibit scar tissue formation. The implant of the present invention may be modified, or used in combination with materials to make it antibacterial, such as, but not limited to, electroplating or plasma spraying with silver ions or other substance. Any of these materials as appropriate may be used at any time after the implant(s) are inserted.

There is disclosed in the above description and the drawing, implants which fully and effectively accomplish the objectives of this invention. However, it will be apparent that variations and modifications of the disclosed embodiments may be made without departing from the principles of the invention. The presentation of the preferred embodiments herein is offered by way of example only and not limitation, with a true scope and spirit of the invention being indicated by the following claims.

What is claimed is:

1. A flanged interbody spinal fusion implant for insertion at least in part between adjacent vertebral bodies adjacent a disc space to be fused and in part along the anterior aspects of the vertebral bodies adjacent that disc space, said implant comprising:

opposed upper and lower surfaces adapted to contact each of the adjacent vertebral bodies, respectively, from within the disc space, said opposed upper and lower surfaces each having at least one opening, said openings being adapted to permit bone growth from adjacent vertebral body to adjacent vertebral body through said implant;

a leading end for insertion between the adjacent vertebral bodies:

a trailing end opposite said leading end, said trailing end including a flanged portion sized to not fit within the disc space between the adjacent vertebral bodies, said flanged portion adapted to overlie at least a portion of the anterior aspects of the adjacent vertebral bodies adjacent the disc space, said flanged portion having a maximum height greater than the maximum height of the remainder of said implant as measured from said upper surface to said lower surface when used within the disc space;

at least two bone screw receiving holes extending through said flanged portion, each of said bone screw receiving holes being adapted to receive a bone screw for engaging said flanged portion to one of the adjacent vertebral bodies, at least one of each of said bone screw receiving holes being oriented in said flanged portion to overlie the anterior aspect of the adjacent vertebral bodies, respectively, adjacent the disc space to be fused; and at least one locking element for locking at least one of the at least two bone screws adapted to be inserted in said at least two bone screw receiving holes, respectively, said at least one locking element being slideable along said trailing end from an initial position that permits the insertion of a bone screw into a respective one of said bone screw receiving holes to a final position that is adapted to retain at least one bone screw to said implant, said at least one locking element having a maximum dimension not exceeding the maximum height of said flanged portion when said locking element is in any position relative to said flange.

2. The implant of claim 1, wherein said trailing end is curved at least in part.

3. The implant of claim 1, wherein said locking element is adapted to be coupled to said implant prior to the insertion of the bone screws into said bone screw receiving holes.

4. The implant of claim 1, wherein said locking element in said final position is adapted to retain at least two bone screws to said implant.

5. The implant of claim 1, wherein said locking element is adapted to slide over at least a portion of at least two of the bone screws in said bone screw receiving holes.

6. The implant of claim 1, wherein said locking element is removably coupled to said implant.

7. The implant of claim 1, wherein said locking element comprises at least one of a screw, a rivet, a cap, and a cover for contacting at least in part a portion of a trailing end of one of the screws inserted into one of said bone screw receiving holes.

8. The implant of claim 1, wherein said locking element is configured to lock only a single one of the bone screws inserted in one of said at least two bone screw receiving holes.

9. The implant of claim 1, wherein said at least two bone screw receiving holes are adapted to position bone screws in a convergent relationship to one another.

10. The implant of claim 1, wherein said at least two bone screw receiving holes are adapted to position bone screws in a divergent relationship to one another.

11. The implant of claim 1, further comprising at least one bone screw having a leading end for placement in the vertebral body and a trailing end opposite said leading end adapted to cooperatively engage said implant so as to prevent the further advancement of the screw into the bone and to be retained within one of said bone screw receiving holes of said implant.

12. The implant of claim 1, wherein said implant comprises at least one of the following materials: metal, titanium, plastic, and ceramic.

13. The implant of claim 1, wherein said implant has an interior surface and a hollow defined therein.

14. The implant of claim 1, in combination with a chemical substance to inhibit scar formation.

15. The implant of claim 1, in combination with an antimicrobial material.

16. The implant of claim 1, in combination with a bone growth promoting material.

17. The implant of claim 16, wherein said bone growth promoting material is at least one of bone, bone morphogenetic protein, hydroxyapatite, and genes coding for the production of bone.

18. The implant of claim 1, in combination with an insertion instrument adapted to cooperatively engage at least a portion of said implant.

19. The implant of claim 1, in combination with a guide having a passage for guiding a bone hole forming device therethrough, said guide having an end adapted to cooperatively engage at least one of said bone screw receiving holes.

20. The implant and guide combination of claim 19, further in combination with a bone hole forming device.

21. The implant and guide combination of claim 20, wherein said bone hole forming device includes one of a drill, a reamer, and a hole punch.

22. A flanged interbody spinal fusion implant for insertion at least in part between adjacent vertebral bodies adjacent a disc space to be fused and in part along the anterior aspects of the vertebral bodies adjacent that disc space, said implant comprising:

opposed upper and lower surfaces adapted to contact each of the adjacent vertebral bodies, respectively, from within the disc space;

a leading end for insertion between the adjacent vertebral bodies;

a trailing end opposite said leading end, said trailing end including a flanged portion sized to not fit within the disc space between the adjacent vertebral bodies, said flanged portion adapted to overlie at least a portion of the anterior aspects of the adjacent vertebral bodies adjacent the disc space, said flanged portion having a maximum height greater than the maximum height of the remainder of said implant as measured from said upper surface to said lower surface when used within the disc space;

said implant having a maximum width that is greater than one-half of the width of the adjacent vertebral bodies into which said implant is adapted to be inserted, said leading end forming at least a portion of a first circle along the width of said implant, said trailing end forming at least a portion of a second circle along the width of said implant, the second circle having a radius greater than the radius of the first circle; and at least two bone screw receiving holes extending through said flanged portion, each of said bone screw receiving holes being adapted to receive a bone screw for engaging said flanged portion to one of the adjacent vertebral bodies, at least one of each of said bone screw receiving holes being oriented in said flanged portion to overlie the anterior aspect of the adjacent vertebral bodies, respectively, adjacent the disc space to be fused.

23. The implant of claim 22, further comprising at least one locking element for locking at least one of at least two bone screws adapted to be inserted in said at least two bone screw receiving holes, respectively, said at least one locking element being moveable from an initial position that permits the insertion of one of the bone screws into a respective one of said bone screw receiving holes to a final position that is adapted to retain at least one of the bone screws to said implant.

24. The implant of claim 23, wherein said locking element is adapted to be coupled to said implant prior to the insertion of the bone screws into said bone screw receiving holes.

25. The implant of claim 23, wherein said locking element in said final position is adapted to retain at least two bone screws to said implant.

26. The implant of claim 23, wherein said locking element is adapted to slide over at least a portion of at least two of the bone screws in said bone screw receiving holes.

27. The implant of claim 23, wherein said locking element is removably coupled to said implant.

28. The implant of claim 23, wherein said locking element comprises at least one of a screw, a rivet, a cap, and a cover for contacting at least in part a portion of a trailing end of one of the screws inserted into one of said bone screw receiving holes.

29. The implant of claim 23, wherein said locking element is configured to lock only a single one of the bone screws inserted in one of said at least two bone screw receiving holes.

30. The implant of claim 22, wherein said at least two bone screw receiving holes are adapted to position bone screws in a convergent relationship to one another.

31. The implant of claim 22, wherein said at least two bone screw receiving holes are adapted to position bone screws in a divergent relationship to one another.

32. The implant of claim 22, further comprising at least one bone screw having a leading end for placement in the vertebral body and a trailing end opposite said leading end adapted to cooperatively engage said implant so as to prevent the further advancement of the screw into the bone and to be retained within one of said bone screw receiving holes of said implant.

33. The implant of claim 22, wherein said implant comprises at least one of the following materials: metal, titanium, plastic, and ceramic.

34. The implant of claim 22, wherein said implant has an interior surface and a hollow defined therein.

35. The implant of claim 22, in combination with a chemical substance to inhibit scar formation.

36. The implant of claim 22, in combination with an antimicrobial material.

37. The implant of claim 22, in combination with a bone growth promoting material.

38. The implant of claim 37, wherein said bone growth promoting material is at least one of bone, bone morphogenetic protein, hydroxyapatite, and genes coding for the production of bone.

39. The implant of claim 22, in combination with an insertion instrument adapted to cooperatively engage at least a portion of said implant.

40. The implant of claim 22, in combination with a guide having a passage for guiding a bone hole forming device therethrough, said guide having an end adapted to cooperatively engage at least one of said bone screw receiving holes.

41. The implant and guide combination of claim 40, further in combination with a bone hole forming device.

42. The implant and guide combination of claim 41, wherein said bone hole forming device includes one of a drill, a reamer, and a hole punch.

43. A flanged interbody spinal implant for insertion at least in part between adjacent vertebral bodies adjacent a disc space to be fused and in part along the anterior aspects of the vertebral bodies adjacent that disc space, said implant comprising:

a maximum width that is greater than one-half of the width of the adjacent vertebral bodies into which said implant is adapted to be inserted;

opposed upper and lower surfaces adapted to contact each of the adjacent vertebral bodies, respectively, from within the disc space, each of said upper and lower surfaces including an opening having a maximum width greater than one-half the maximum width of said implant;

a leading end for insertion between the adjacent vertebral bodies, said leading end forming at least a portion of a circle;

a trailing end opposite said leading end and a mid-longitudinal axis through said leading and trailing ends, said trailing end including a flanged portion sized to not fit within the disc space between the adjacent vertebral bodies, said flanged portion adapted to overlie at least a portion of the anterior aspects of the adjacent vertebral bodies adjacent the disc space, said flanged portion having a height greater than the maximum height of the remainder of said implant as measured from said upper surface to said lower surface when used within the disc space;

opposite sides between said trailing and leading ends, said sides being substantially parallel to the mid-longitudinal axis along a substantial portion of the length of said implant, each of said opposite sides including an exterior surface having a non-curved portion in a plane parallel to the mid-longitudinal axis of said implant;

at least two bone screw receiving holes extending through said flanged portion, each of said bone screw receiving holes being adapted to receive a bone screw for engaging said flanged portion to one of the adjacent vertebral bodies, at least one of each of said bone screw receiving holes being oriented in said flanged portion to overlie the anterior aspect of the vertebral bodies, respectively, adjacent the disc space to be and at least one locking element for locking at least one of at least two bone screws adapted to be inserted in said at least two bone screw receiving holes, respectively, said at least one locking element being moveable from an initial position that permits the insertion of one of the bone screws into a respective one of said bone screw receiving holes to a final position that is adapted to retain at least one of the bone screws to said implant, said locking element being adapted to be coupled to said implant prior to the insertion of the bone screws into said bone screw receiving holes.

44. The implant of claim 43, wherein said openings of said upper and lower surfaces are in communication with one another to define a generally open interior of said implant.

45. The implant of claim 43, wherein said locking element in said final position is adapted to retain at least two bone screws to said implant.

46. The implant of claim 43, wherein said locking element is adapted to slide over at least a portion of at least two of the bone screws in said bone screw receiving holes.

47. The implant of claim 43, wherein said locking element is removably coupled to said implant.

48. The implant of claim 43, wherein said locking element comprises at least one of a screw, a rivet, a cap, and a cover for contacting at least in part a portion of a trailing end of one of the screws inserted into one of said bone screw receiving holes.

49. The implant of claim 43, wherein said locking element is configured to lock only a single one of the bone screws inserted in one of said at least two bone screw receiving holes.

50. The implant of claim 43, wherein said at least two bone screw receiving holes are adapted to position bone screws in a convergent relationship to one another.

51. The implant of claim 43, wherein said at least two bone screw receiving holes are adapted to position bone screws in a divergent relationship to one another.

52. The implant of claim 43, further comprising at least one bone screw having a leading end for placement in the vertebral body and a trailing end opposite said leading end adapted to cooperatively engage said implant so as to prevent the further advancement of the screw into the bone and to be retained within one of said bone screw receiving holes of said implant.

53. The implant of claim 43, wherein said implant comprises at least one of the following materials: metal, titanium, plastic, and ceramic.

54. The implant of claim 43, wherein said implant has an interior surface and a hollow defined therein.

55. The implant of claim 43, in combination with a chemical substance to inhibit scar formation.

56. The implant of claim 43, in combination with an antimicrobial material.

57. The implant of claim 43, in combination with a bone growth promoting material.

58. The implant of claim 57, wherein said bone growth promoting material is at least one of bone, bone morphogenetic protein, hydroxyapatite, and genes coding for the production of bone.

59. The implant of claim 43, in combination with an insertion instrument adapted to cooperatively engage at least a portion of said implant.

60. The implant of claim 43, in combination with a guide having a passage for guiding a bone hole forming device therethrough, said guide having an end adapted to cooperatively engage at least one of said bone screw receiving holes.

61. The implant and guide combination of claim 60, further in combination with a bone hole forming device.

62. The implant and guide combination of claim 61, wherein said bane hole forming device includes one of a drill, a reamer, and a hole punch.

63. The implant of claim 13, wherein at least one of said bone screw receiving holes is configured to permit at least a portion of a bone screw to pass through said hollow of said implant.

64. The implant of claim 34, wherein at least one of said bone screw receiving holes is configured to permit at least a portion of a bone screw to pass through said hollow of said implant.

65. The implant of claim 44, wherein at least one of said bone screw receiving holes is configured to permit at least a portion of a bone screw to pass through said interior of said implant.

66. The implant of claim 22, wherein said flanged portion of said trailing end has a maximum width generally the same as the maximum width of said implant.

67. The implant of claim 43, wherein said flanged portion of said trailing end has a maximum width generally the same as the maximum width of said implant.

\* \* \* \* \*

UNITED STATES PATENT AND TRADEMARK OFFICE
CERTIFICATE OF CORRECTION

PATENT NO.         : 7,163,561 B2                                     Page 1 of 1
APPLICATION NO. : 10/838933
DATED              : January 16, 2007
INVENTOR(S)        : Gary K. Michelson It is certified that error appears in the above-identified patent and that said Letters Patent is hereby corrected as shown below:

Column 11, line 24:
Change "bodies:" to -- bodies; --.

Column 14, line 64:
Change "be and" to -- be fused; and --.

Column 16, line 23:
Change "bane" to -- bone --.

Signed and Sealed this

Twenty-seventh Day of March, 2007

JON W. DUDAS
*Director of the United States Patent and Trademark Office*